(12) United States Patent
Wilson et al.

(10) Patent No.: US 7,242,009 B1
(45) Date of Patent: Jul. 10, 2007

(54) METHODS AND SYSTEMS FOR SIGNAL PROCESSING IN PARTICLE DETECTION SYSTEMS

(75) Inventors: Geoffrey Wilson, Rogue River, OR (US); James Brady, Ashland, OR (US)

(73) Assignee: Hach Ultra Analytics, Inc., Grants Pass, OR (US)

( * ) Notice: Subject to any disclaimer, the term of this patent is extended or adjusted under 35 U.S.C. 154(b) by 231 days.

(21) Appl. No.: 11/158,491

(22) Filed: Jun. 22, 2005

(51) Int. Cl.
*G01N 21/64* (2006.01)
(52) U.S. Cl. .................................. 250/461.1
(58) Field of Classification Search ... 250/458.1–461.1
See application file for complete search history.

(56) References Cited

U.S. PATENT DOCUMENTS

| | | | |
|---|---|---|---|
| 5,668,373 A | 9/1997 | Robbat, Jr. et al. | 250/339.12 |
| 5,701,012 A | 12/1997 | Ho | 250/461.2 |
| 5,895,922 A | 4/1999 | Ho | 250/491.2 |
| 6,111,642 A | 8/2000 | DeFreeze et al. | 356/377 |
| 6,490,530 B1 | 12/2002 | Wyatt | 702/24 |
| 6,532,067 B1 | 3/2003 | Chang et al. | 356/318 |
| 6,584,413 B1 | 6/2003 | Keenan et al. | 702/28 |
| 6,593,582 B2 | 7/2003 | Lee et al. | 250/458.1 |
| 6,603,546 B1 * | 8/2003 | Barbieri et al. | 356/318 |
| 6,618,712 B1 | 9/2003 | Parker et al. | 706/15 |
| 6,675,106 B1 | 1/2004 | Keenan et al. | 702/28 |
| 6,831,279 B2 | 12/2004 | Ho | 250/458.1 |
| 6,885,440 B2 | 4/2005 | Silcott et al. | 356/73 |
| 2002/0175294 A1 | 11/2002 | Lee et al. | 250/458.1 |
| 2003/0114986 A1 | 6/2003 | Padmanabhan et al. | 702/1 |
| 2003/0139886 A1 | 7/2003 | Bodzin et al. | 702/28 |
| 2004/0010379 A1 | 1/2004 | Craig et al. | 702/22 |
| 2004/0064260 A1 | 4/2004 | Padmanabhan et al. | 702/19 |
| 2004/0125371 A1 | 7/2004 | Chang et al. | 356/318 |
| 2004/0232052 A1 | 11/2004 | Call et al. | 209/143 |
| 2004/0238756 A1 * | 12/2004 | Rigler et al. | 250/458.1 |
| 2005/0070025 A1 | 3/2005 | Mooradian et al. | 436/178 |
| 2005/0073683 A1 | 4/2005 | Gard et al. | 356/337 |
| 2006/0231771 A1 * | 10/2006 | Lee et al. | 250/458.1 |

OTHER PUBLICATIONS

Biral, *Real-time biological agent detection using particle size, shape and fluorescence characterisation agent*, http://www.armedforces-int.com/print.asp?artID=2445, p. 1-8 Apr. 27, 2005).

(Continued)

*Primary Examiner*—David Porta
*Assistant Examiner*—Christopher Webb
(74) *Attorney, Agent, or Firm*—Stoel Rives LLP; Matthew S. Bethards

(57) ABSTRACT

A method for statistically distinguishing between two or more populations, such as between samples containing background and threat particles, is disclosed. According to one embodiment, the method for statistically distinguishing is a method for processing a signal in a particle detection system. The method may include characterizing each particle detected by a signal vector. The method may further include calculating a weight of each particle detected using a weighting function of the signal vectors. The weighting function may be a functional of a threat particle probability distribution and a background particle probability distribution. The method may also include summing a total weight of all particles tested and generating an alarm signal if the total weight exceeds an alarm level.

21 Claims, 10 Drawing Sheets

OTHER PUBLICATIONS

The National Academies Press, *Sensor Systems for Biological Agent Attacks: Protecting Buildings and Military Bases* (2005), Board on Manufacturing and Engineering Design (*BME*), http://www.nap.edu/books/030909576X/html, pp. 1-2 (Apr. 27, 2005).

Luoma, et al., "A Fluorescence Particle Detector for Real Time Quantification of Viable Organisms in Air", Proceeding of SPIE, vol. 4576 (2002).

National Research Council, Sensor Systems for Biological Attack Agents (2005) National Academies Press, Washington DC (Ch. 4-5).

Sivaprakasam, et al., "Multiple UV Wavelength Excitation and Fluorescence of Bioaerosols", Sep. 20, 2004, vol. 12, No. 19, Optics Express 4457-4466.

Wilson et al., "Advances in BioLert Diode Laser Based Laser Induced Fluorescence Bio-Particle Sensors", (Sep. 14, 2004) Hach Ultra Analytics.

Wilson, et al., "Autofluorescence Detection Using UV Diode Laser Simultaneous Excitation of Multiple Wavelengths", Proceedings of SPIE, vol. 5071 (Sep. 2003) pp. 253-263.

Wilson et al., "Design Considerations and Signal Processing Algorithms for Laser-Induced Fluorescence Airborne Pathogen Sensors", Optically Based biological and chemical Sensing for Defence, Proceedings of SPIE vol. 5617 (SPIE, Bellingham) (Published after Oct. 25, 2004).

Wilson et al., "Diode Laser Induced Fluorescence Biological Particle Sensor", (Hach Ultra Analytics, Jan. 2005).

Wilson et al., "Improving Diode-Laser-Induced Fluorescence Detection of Airborne Biological Particles by Exciting Multiple Biofluorophores", Proceedings of SPIE, vol. 5416, Chemical and Biological Sensing V, Aug. 2004, pp. 157-167.

Wilson et al., "Multispectral Diode Laser Induced Fluorescence Biological Particle Sensor", Optically Based Biological and Chemical Sensing for Defence, Proceedings of SPIE vol. 5617 (SPIE, Bellingham, WA, 2004).

Wilson et al., "Optimally Weithted Degree of Threat Algorithm for Laser-Induced Fluorescence Biological Particle Sensors", Presented at ROC curve workshop (Jul. 28, 2004).

Wilson, et al., "Receiver Operator Characteristic (ROC) Curves for Laser Induced Fluorescence (LIF) Biological Particle Sensors", Presented at 2004 Scientific conference on Obscuration & Aerosol Research (Jun. 23, 2004).

* cited by examiner

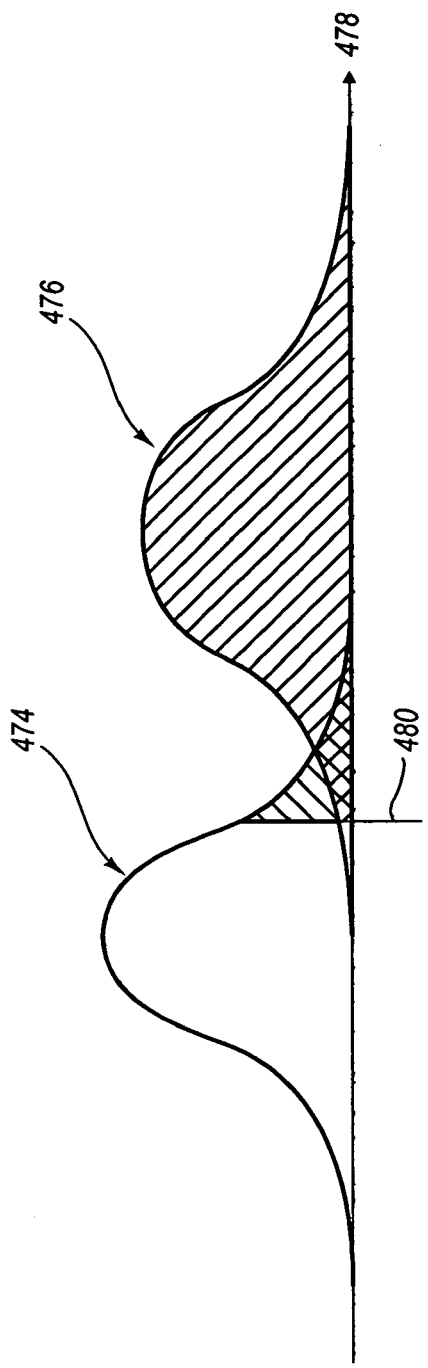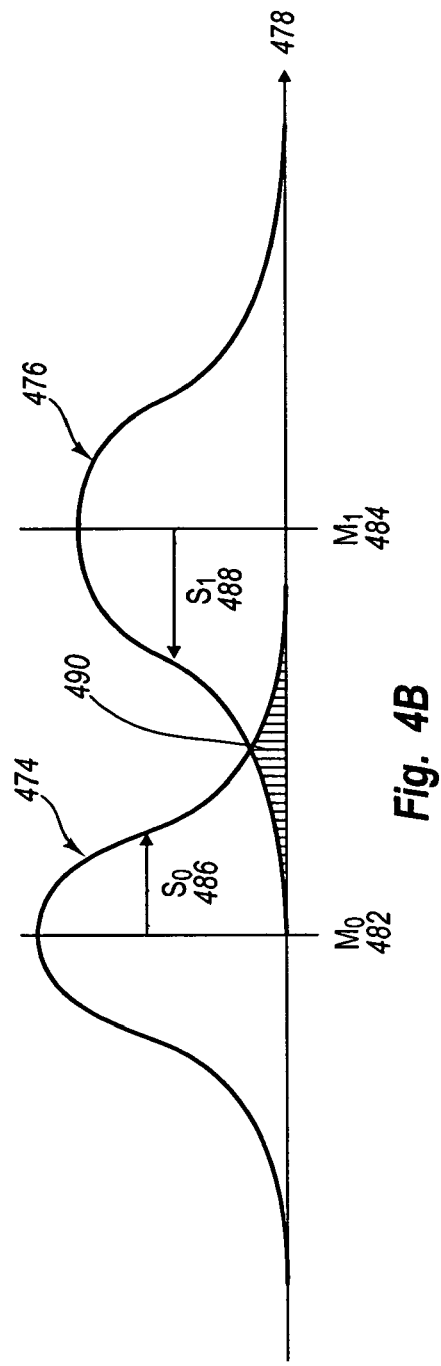
Fig. 4A
Fig. 4B

Bacillus Globigii

*Fig. 9A*

Kaolin

*Fig. 9B*

METHODS AND SYSTEMS FOR SIGNAL PROCESSING IN PARTICLE DETECTION SYSTEMS

FEDERALLY SPONSORED RESEARCH OR DEVELOPMENT

Work on this invention was carried out under Defense Advanced Research Projects Agency ("DARPA") Microsystems Technology Office contract No. N66001-02-C-8016 in support of a program entitled Semiconductor Ultraviolet Optical Sources ("SUVOS"). The government has certain rights in the invention.

TECHNICAL FIELD

The examples in this disclosure arise from research in signal processing in particle detection systems that use laser-induced fluorescence ("LIF") to identify samples of an air stream that may contain particles of interest, such as potentially viable biological particles.

BACKGROUND INFORMATION

Contamination control, including particulate monitoring, plays a role in the manufacturing processes of several industries. These industries require clean rooms or clean zones with active air filtration and require the supply of clean raw materials such as process gases, de-ionized water, chemicals, and substrates. In the pharmaceutical industry, the Food and Drug Administration requires particulate monitoring because of the correlation between detected particles in an aseptic environment and viable particles that contaminate the product produced.

Recent attention has been given to the monitoring and detection of biological agents. If aerosolized agents (biological particles) are introduced into an environment and are within the respirable range of particle sizes, then the biological particles may deposit in human lungs resulting in illness or death.

Biological contamination can occur not only in open air, but also in confined spaces, such as postal handling equipment, aircraft, hospitals, water supplies, and air ducts. Minimizing the introduction of biological particles in an environment requires the fast detection of possible pathogens. Laser-induced fluorescence of fluorescent biological substances (biofluorophores) provides a real-time technique for initially identifying samples that are candidates for containing airborne pathogens such as aerosolized bacterial spores and viruses. LIF thus may be used as a first, or detect-to-warn, stage in a biohazard detection system, with slower, but more specific tests, such as nucleic acid sequencing and/or culturing, used as additional steps or stages.

Biofluorophores significant to LIF include, tryptophan, NADH, and riboflavin or other flavinoids. But many more or less innocuous natural and man-made airborne particles also fluoresce. Consequently, some LIF systems (or "sensors") may find it hard to distinguish harmless particles from particles of interest, like pathogens. LIF sensors are thus vulnerable to false positives—the sensor incorrectly signals the presence of threat particles. False positives can be reduced by reducing the sensitivity of the sensor to possible threat particles, but this reduces the true positive rate.

Since LIF detection of biological particles was first proposed, resources have been invested in efforts to improve hardware—like the lasers, optics, and detectors. But less effort has gone into signal processing and software. Some LIF sensors use a "region of threat" ("RoT") approach. As each particle is detected, the sensor characterizes the particle based on fluorescence and decides whether it falls within the region of threat. If the particle falls within that region, the system counts it as a threat particle. The RoT sensor accumulates the count for a sample interval. The system senses a signal—like an alarm signal—indicating whether a threshold—like an alarm threshold—has been exceeded by the sample, and therefore whether the sample is a sample of interest. A RoT system tests the threshold against the accumulated count.

The Region of Threat approach may use a particle probability-distribution data to define the region of threat. Each of FIG. 9A and FIG. 9B is a graph of data for a large number of particles—particle spectral probability distribution data. Each particle is characterized by two-dimensional normalized fluorescence: the G/E axis represents green fluorescence normalized by elastic scatter, the B/E axis represent blue fluorescence normalized by elastic scatter. Each individual particle can be numerically characterized by a blue-green fluorescence vector, represented in FIG. 9A and FIG. 9B by a particle's location in fluorescent color space—the G/E—B/E plane. The vertical axis represents the normalized number of particles for each vector, sometimes called the bin occupancy. These figures show graphs of data for, respectively, (a) *Bacillus globigii*, which may be a particle of interest, and (b) kaolin, which may be a background particle. Each figure shows data for about 30,000 particles.

FIG. 8 shows an example Region of Threat. Any particle whose fluorescence falls within the RoT is treated as a threat particle; any particle whose fluorescence is outside that region is treated as background.

RoT sensors may be configured to generate an alarm based on a single particle within the region of threat. RoT sensors also may be configured to generate an alarm based on the number of threat particles detected during a sample interval. During the sample interval, the sensor counts the number of particles within the RoT. At the end of the sample interval, if the presumed threat count exceeds a preset threshold, the system sends a signal.

The RoT approach judges each particle to be a threat or not. Because some background particles may have the same fluorescence as some actual threat particles, it is not always possible to make a correct decision about each particle. Thus, the RoT approach may detect some actual background particles as presumed threat particles, and some actual threat particles as background particles. Moreover, treating each presumed threat particle identically is unlikely to be an optimal way of differentiating samples, and thus is unlikely to have an optimal probability of false positive differentiation.

Furthermore, the RoT is hard to extend to multiple dimensions. A rectangular RoT approach may be simple to implement, but may not optimally fit the actual spectral distribution of threat particles. Some regions of small threat probability may be included, while other regions of larger probability may be left out. Moreover, innocuous background materials with nearby spectral distributions may not be optimally rejected, particularly if their centroids lie obliquely to that of the threat, relative to the coordinate axes. An alternative is to define a complexly shaped RoT, but this may be computationally awkward.

Moreover, a different RoT usually must be defined for each pair of threat and background materials. Rejection of the largely unknown background is not well controlled, and no native mechanism is provided for adapting to a changing background. Instead, this is often provided ad hoc using an adaptive alarm level, which allows prescribing neither the level of detection of the threat, or the false positive rate of the background.

RoT sensors may use a time measurement to decide whether a complete sample has been acquired. Time-based sampling may be vulnerable to fluctuations in background particle concentration. (These concentrations have been observed to vary over two orders of magnitude for some applications.) For instance, consider a device that mistakes 1% of background particles for threat particles, and that alarms if 100 or more threat particles per sample are detected. If the background particle concentration is such that 1000 particles are acquired during the sample time interval, then only 10 background particles per sample are counted as threats, and the sensor will correctly not alarm. But if the background concentration increases by 100× (two orders of magnitude), then about 1000 background particles will be mistaken for threats, and the device will falsely alarm (a false positive).

BRIEF DESCRIPTION OF THE DRAWINGS

FIG. 4A is a graphical representation of a sample background weight probability distribution and a sample threat-present weight-probability distribution;

FIG. 4B is a graphical representation of an overlap integral of the sample background weight-probability distribution and the sample threat-present weight probability distribution of FIG. 4A;

FIG. 9A is a histogram of a particle of interest.

FIG. 9B is a histogram of a particle that is not a particle of interest.

DETAILED DESCRIPTION OF EMBODIMENTS

Figure 1:
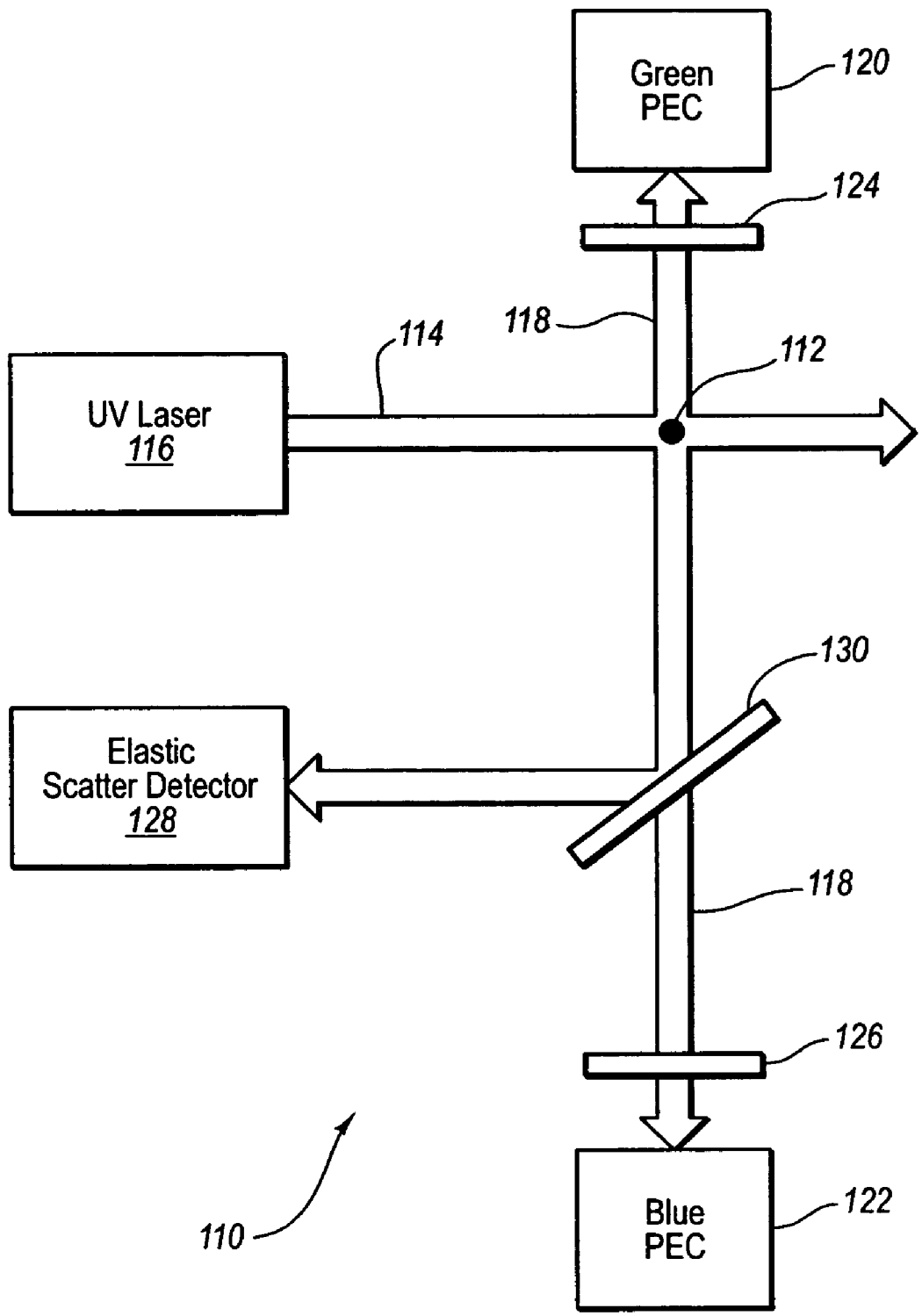
FIG. 1 is an optical schematic block diagram representing a dual fluorescence band photoelectron counting sensor according to one embodiment of a particle sensor.

FIG. 1 is a schematic block diagram of one embodiment of an optical particle sensor 110, namely a dual fluorescence band photoelectron counting sensor 110, a kind of LIF system.

Hardware

LIF sensor 110 views the fluorescence of particles in an air stream 112 as they are irradiated by an ultraviolet ("UV") beam 114. Excitation beam 114 is generated by a UV laser 116. A variety of excitation light sources may be used, as is apparent to those skilled in the art. For example, the UV laser 116 may be a single UV diode laser. Continuously emitting diode lasers may be used to increase particle-counting efficiency, allow the sizing of particles, and reduce sensor cost and complexity. The light source may be a pulsed solid-state laser. UV Laser 116 may be a dual diode laser beam-combining module, which combines laser emissions at multiple wavelengths, such as 375 nanometers and 405 nanometers, into one beam. Using multiple excitation frequencies may excite biofluorophores with different absorption spectra, which may improve the sensor's specificity. Single or multiple light emitting diodes ("LEDs") may be used. Multiple light sources may also be used without being combined into a single beam.

The LIF sensor may detect fluorescence emission 118 of an irradiated particle. Various particles may have similar emission spectra, particularly when excited at a relatively long wavelength. To resolve the emission spectra, LIF sensor 110 may use separate fluorescence detectors 120, 122 having respective bandpass filters 124, 126.

In the example, one detector is a photoelectron counter ("PEC") 120 equipped with a bandpass filter 124 transmitting green light. For example, the green bandpass filter 124 could pass wavelengths in a range of about 500 to 540 nanometers. A second detector may also be a PEC 122 equipped with a bandpass filter 126 that transmits blue light. The blue bandpass filter 126 may pass wavelengths in a range from about 420 to 480 nanometers. PEC detectors 120, 122 may be Hamamatsu 7155 photon counting PMT modules. Alternative or additional detectors may be used. One example is photomultiplier tubes ("PMTs") in analog mode where the individual photoelectron bursts are integrated into a slowly varying pulse, whose height or area characterizes the particle fluorescence. Alternatively, sensor 110 could replace multiple detectors with a single multiple-pixel detector in which all spectral bands share a common aperture and are dispersed onto the detector through a diffraction grating, such as a Hamamatsu R5900-L16. For instance, the Hach Ultra Analytics "BioLert 2×16C5+1" uses a 16 pixel PMT that counts fluorescence photoelectrons in each of 16 spectral bands. A single multiple-pixel detector may avoid complicated, bulky, and expensive spectral demultiplexing schemes involving dichroic beamsplitters.

LIF sensor 110 acquires elastic scattering information from elastic scatter detector 128. Dichroic beamsplitter 130 selectively transmits, to elastic scatter detector 128, light scattered by particles 112 light at the UV excitation wavelength. Alternatively, one could use a different frequency and/or separate light source to help generate elastic scatter information. Alternatively, the sensor could use a non-scatter detector, such as a light-obscuration detector, to detect particles regardless of whether they fluoresce.

LIF sensor 110 uses this information in conjunction with the raw fluorescence intensities acquired by detectors 120, 122. Raw fluorescence intensity is proportional to irradiance. Thus, raw fluorescence intensity may vary among identical particles in a real sensor. For instance, excitation beam 114 may contain local "hot spots" or diffraction patterns. This may cause the time-integrated irradiance to vary from particle to particle. Irradiance may also vary between identical particles because of turbulent or otherwise non-ideal airflow. Elastic scattering is also proportional to time-integrated irradiance. Thus, elastic scatter can be used to normalize raw fluorescence and improve the fluorescence resolution for identical particles. Elastic scatter normalization may also reduce the variation among different-sized particles of the same composition. Elastic scatter information may also help distinguish particles with fluorescence properties similar to threats, but with different size distributions. Elastic scatter information can also gate the counting of fluorescence photons.

Figure 2:
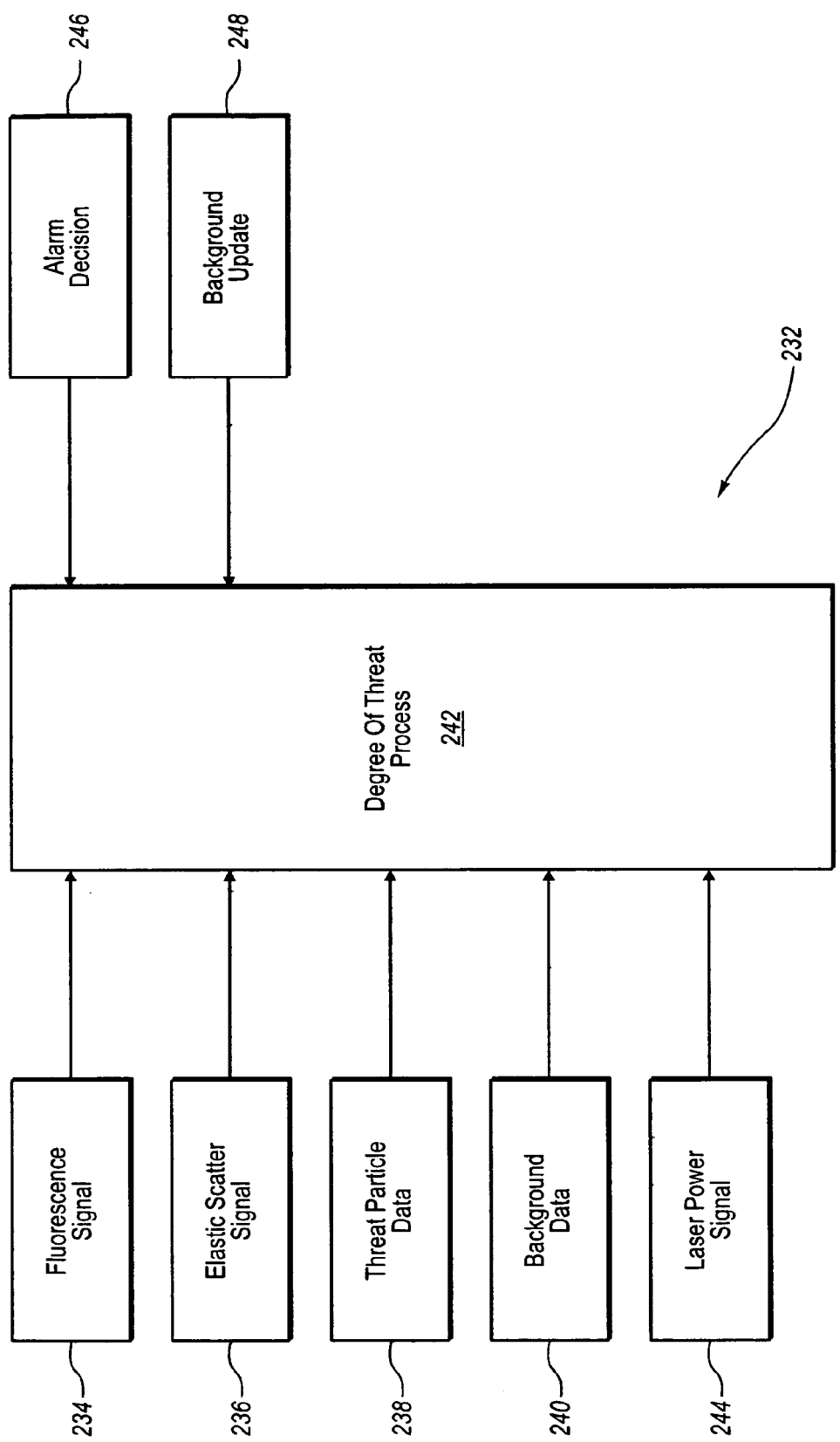
FIG. 2 is a block diagram representing a system for detecting a concentration of hazardous particles against a background of harmless particles.

FIG. 2 is a block diagram of a system 232 for detecting a concentration of particles of interest, such as potential threat particles, against a background of other particles. A fluorescence signal 234 and elastic scatter signal 236, as discussed in conjunction with FIG. 1, may be inputs into the system. System 232 is not limited to LIF applications, optical applications, or biological particle detection. Furthermore, system 232 may use alternative optical or non-optical measurements, such as light scattering, absorption, color, particle volume, particle cross-section, particle shape, electric charge, mass, magnetism, or other detectable information about particles. Moreover, system 232 and the methods described herein may be used to make decisions based on distinguishing between two populations of any kind having differing statistics based on signals generated by the appropriate hardware. For instance, similar systems and methods could be used with applications that analyze particles in a liquid medium, like water, oil, or hydraulic fluid. The analysis could be, for instance, particle counting, sizing, or detection of potential biological particles.

Signal Processing

The Background Information describes the Region-of-Threat approach, which individually judges whether each particle is a threat, and counts the adjudged threat particles. An alternative is the degree of threat ("DoT") approach. The DoT approach defines a weighting function and assigns a weight to detected particles—regardless whether they are threats. The DoT system accumulates the weights of all weighted particles for a sample. Like an RoT system, a DoT system decides if a sample is a sample of interest—whether it contains particles of interest such as threat particles. A DoT sensor makes this decision based on a test of the threshold versus accumulated weight.

The RoT approach can be thought of as a special, degenerate case of DoT—as DoT in which the only assigned weights are 0 and 1. Thus on a particle-by-particle basis, the RoT approach makes a "black-and-white" decision, while DoT (other than the degenerate case), which has a range of more than two possible particle weights, makes a "grey scale" decision. Because it is a special case, RoT is unlikely to be optimal.

The effect of the RoT and DoT approaches can be measured. LIF sensor performance may be characterized by four metrics. (These metrics may also be used to characterize any device or method that distinguishes samples containing items of interest from samples that do not.) The metrics are:

(1) the false positive probability—the probability of concluding that a sample contains threat particles when in fact it contains only background particles: (a) the number of samples incorrectly identified as threats, divided by (b) the total number of samples;

(2) the true positive probability—the probability of detection of the threat; in other words, the likelihood of correctly concluding that a sample contains threat particles: (a) the number of samples correctly identified as threats, divided by (b) the number of actual threat samples.

(3) the level of detection—the smallest quantity of threat particles that can be detected with the other three metrics prescribed; and (4) the response time of the sensor—the time needed to collect enough particles to decide confidently whether threat particles are present.

These four sensor metrics are inter-related, and a subset of them is usually not meaningfully quantified in the absence of the others.

FIGS. 4A and 4B may help illustrate the first two metrics. Each sample has a total weight equaling the sum of the weights of the particles in that sample. Consider the samples that don't contain threat particle—background samples. The samples weights of these samples will not be identical. Rather, they will have a distribution—a background sample total weight probability distribution. Likewise, the weights samples containing threat particles also are distributed—they have a threat-present sample total weight probability distribution.

FIG. 4A shows a background probability distribution 474 of weights of non-threat samples, and a threat-present probability distribution 476 of weights of samples of interest. Horizontal axis 478 represents the accumulated sample weight, and the vertical dimension represents the relative probability. Vertical line 480 represents a threshold. All samples to the right of (with a weight greater than) threshold 480 will test as samples of interest. But some of these samples are actually background samples, and thus are false positives.

These two distributions have an overlap. The overlap has an integral 490, represented in FIG. 4B by the vertically hatched area. If the overlap integral 490 is reduced or minimized, then the probability of false positives is reduced or minimized, for a given true positive probability. A weighting function may reduce or minimize the number of false positives; it may do so by setting weights so that the resulting weight-probability distributions 474 and 476 will have a reduced or minimized overlap integral 490.

For N>>1, the probability distributions 474, 476 may be normal, and therefore may be characterized by a mean ($M_0$) 482, ($M_1$) 484 and standard deviation ($S_0$) 486, ($S_1$) 488. Minimizing the overlap integral 490 is approximately equal to maximizing (a) the square of the difference between the means of the weight probability distributions, divided by the sum of the variances, or $$\frac{(M_1 - M_0)^2}{S_1^2 + S_0^2}.$$ Eq. 4.1

This quantity can be simplified and then reduced, so that it can be maximized by applying Lagrange's method of undetermined multipliers (also called Lagrange multipliers or Lagrangian multipliers) as described in the embodiment below.

Figure 10:
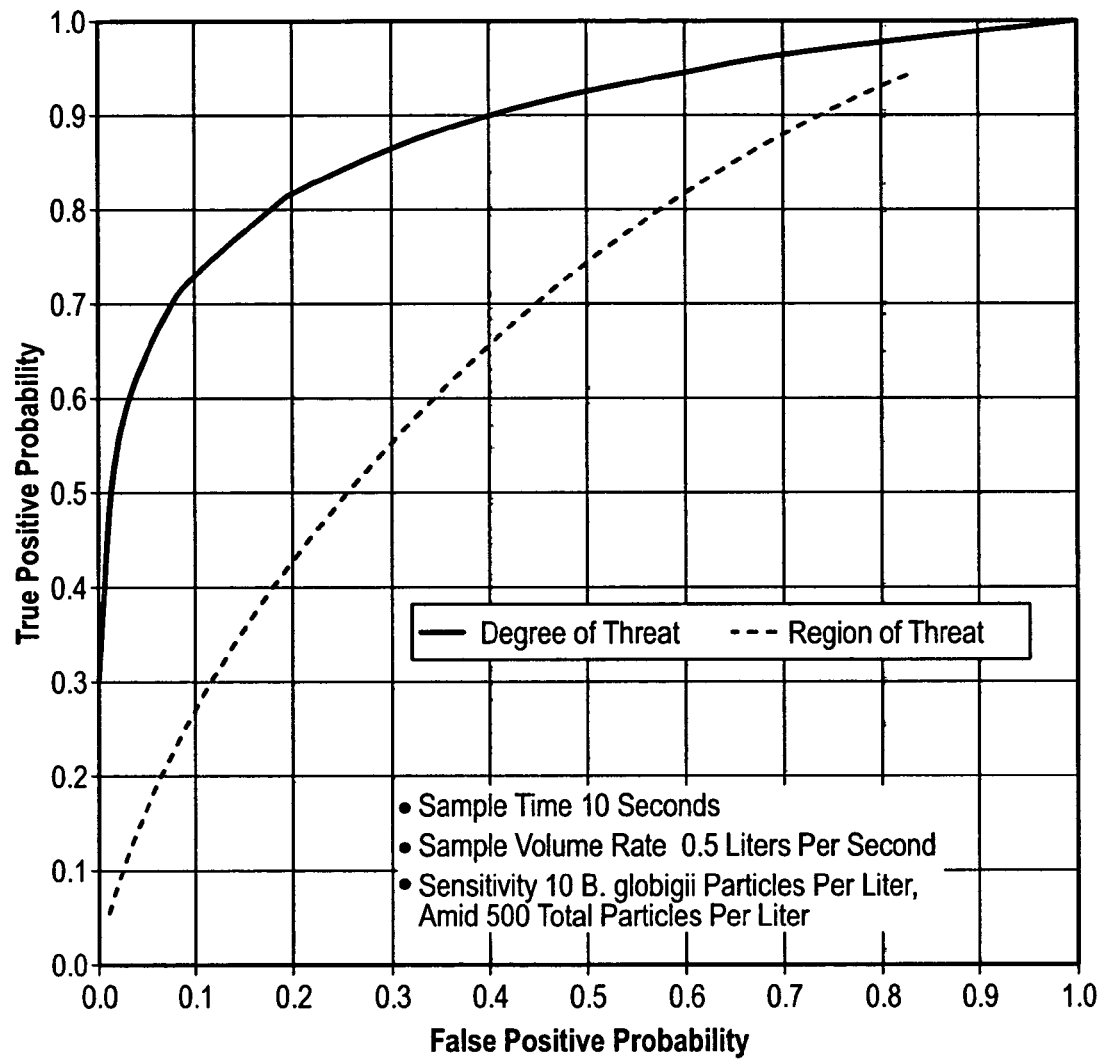
FIG. 10 is a graph showing the false positive probability versus the true positive probability for optimal RoT and optimally weighted DoT curves.
Figure 11:
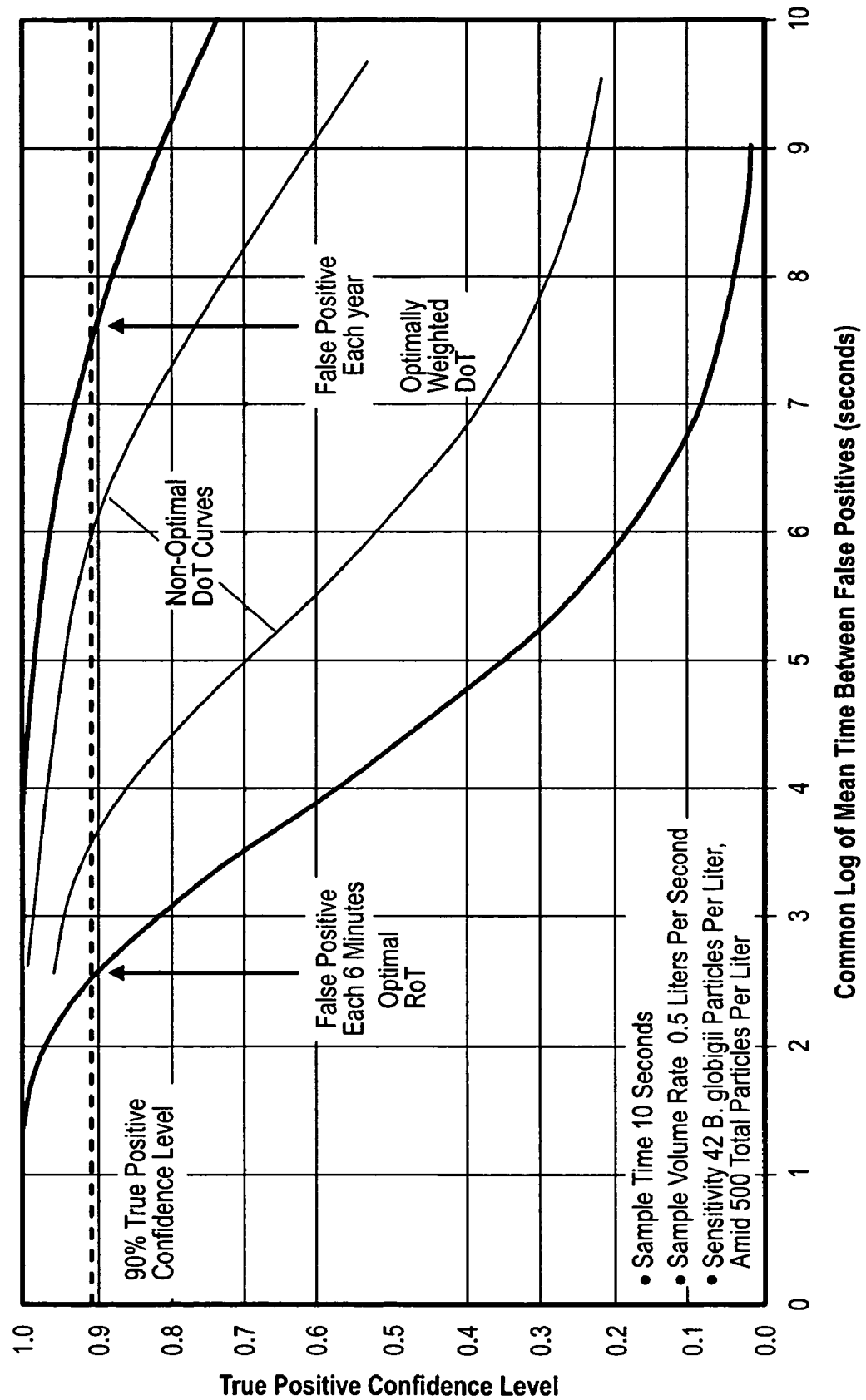
FIG. 11 is a graph showing Time Between False Positives versus True Positive Confidence Level for optimally weighted RoT and DoT curves, and for some non-optimal DoT curves.

FIG. 10 and FIG. 11 each compare the RoT and DoT methods. The curves in FIG. 10 are discrete sampling ROC (receiver operating characteristic) curves. These curves plot true positive probability versus false positive probability, parametized by the threshold or alarm, for a given sensitivity, sample time, and sample volume rate. In more detail, the parameters and their interpretation are:

The sensor alarms if X—the total sample weight—is greater than a threshold A

False positive probability is $P_- = \frac{1}{2}[1-\text{sgn}(A-M_0)\text{erf}(|A-M_0|/2^{1/2}S_0)]$ True positive probability is $P_+ = \frac{1}{2}[1-\text{sgn}(A-M_1)\text{erf}(|A-M_1|/2^{1/2}S_1)]$ Sensitivity is $C_\theta$ (which depends upon background concentration C)

Confidence level is $P_+$

False alarm rate (or false positive rate or FPR) is $P_-/T$

Response time is T

Thus, each discrete sampling ROC curves of FIG. 10 is a plots of $P_+$ versus $P_-$, parameterized by A. It is a functional of a the weighting function W.

The better approach is on the upper left: as shown FIG. 10, an optimally weighted DoT approach has a superior ratio of true positives to false positives. (The sampling variables used to derive this graph are: sample time of 10 second, sample volume rate of 0.5 liters per second, and sensitivity of 10 B. globigii particles, i.e., particles of interest, per liter amid 500 total particles per liter.)

FIG. 11 shows continuous ROC curves. These are plots of confidence level $P_+$ versus false positive rate FPR for a fixed sensitivity $C_\theta$. FIG. 11 includes curves for optimally weighted RoT, optimally weighted DoT, and non-optimally weighted DoT functions. For the particular sampling parameters, a 90% true positive confidence level using an optimal RoT approach one can expect a false positive one per six minutes. But using an optimally weighted DoT approach could reduce false positives to one per year. Even some non-optimally weighted DoT functions yield improved results. (The sampling variables used to derive this graph are: sample time of 10 second, sample volume rate of 0.5 liters per second, and sensitivity of 42 B. globigii particles, i.e., particles of interest, per liter amid 500 total particles per liter. The curves are derived from time-extrapolated sample data. Experiments using the DoT approach in the Hach Ultra Analytics BioLert also indicate a mean time between false positives of one year for a true positive confidence level of 98%, for a sample size of 30,000 particles, a level of detection of respectively, 238 threat particles amid bentonite background particles; 253 threat particles amid diesel soot background particles, and 1388 threat particles amid Johnson grass spore background particles.

Example Method

Figure 3:
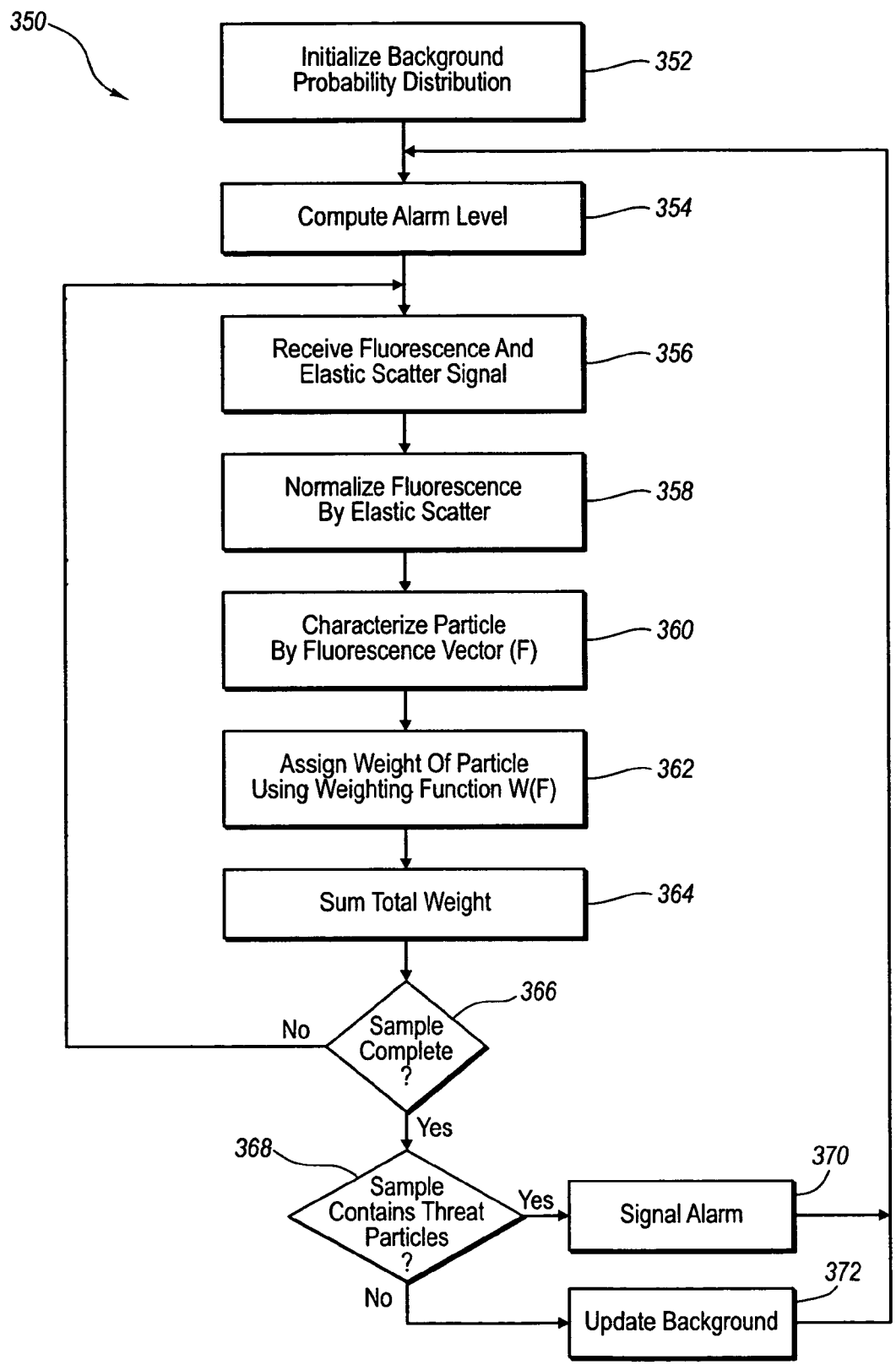
FIG. 3 is a flow diagram representing one embodiment of a method for obtaining and processing a signal in a fluorescence particle detection system.

FIG. 3 is a general flow diagram of an embodiment, using a DoT approach, of a method for processing 350 a signal in a fluorescence particle detection system.

Example method 350 may include the step 352 of initializing a background probability spectral distribution. The method may compute an alarm or threshold for a region of concern, acquire a sample of particles, weight each particle, accumulate the weights in each sample, test the accumulated weights against the threshold, and send a signal based on the results of the test. FIG. 3 shows these as steps 354, 356, 358, 360, 360, 364, 366, 370. The method may also update the background spectral distribution, shown as step 372.

These steps will now be discussed in more detail. Most of these steps include processing of arrays that are representative of fluorescence space. The example assumes a sensor with multiple fluorescence channels, where D=Number of fluorescence channels, and each channel has a number of possible fluorescence levels (also called the "mesh resolution") where n=the number of levels per fluorescent channel.

Figure 8:
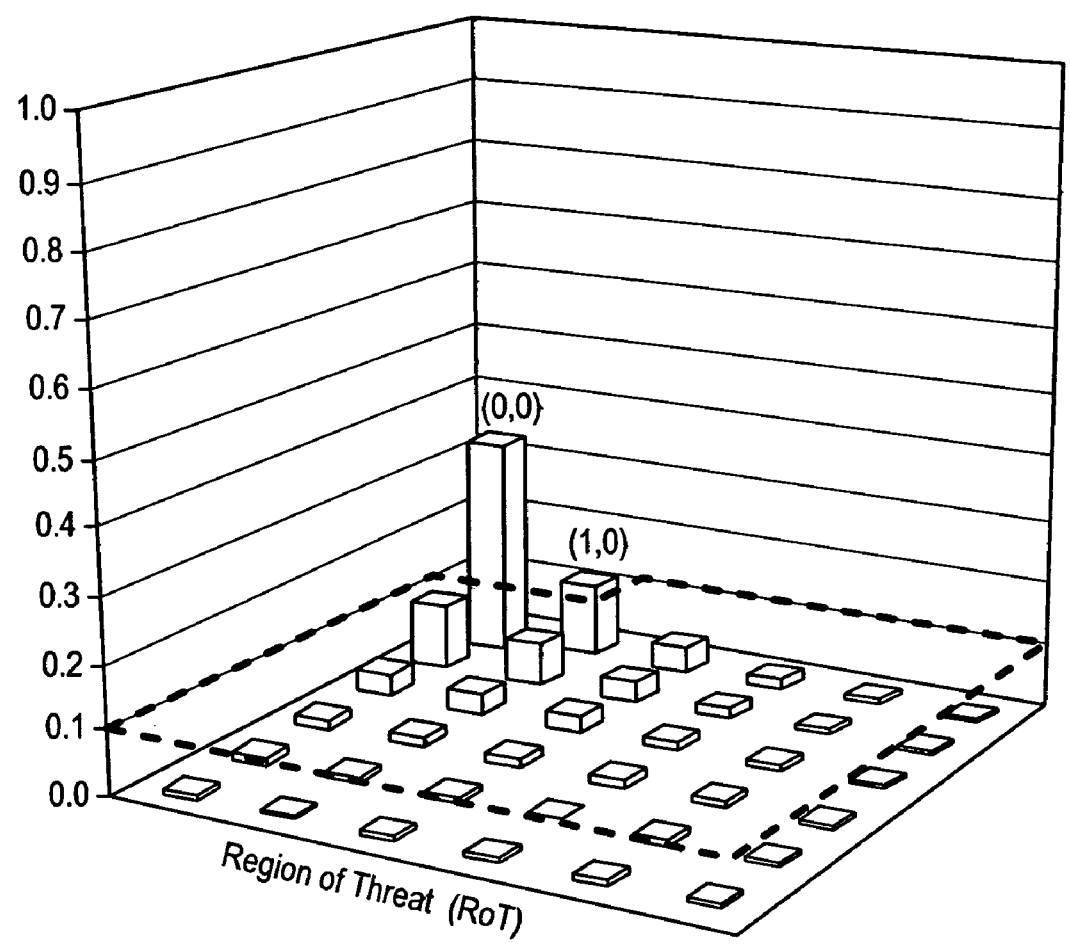
FIG. 8 is a histogram of showing an example of a Region of Threat.
Figures 9A, 9B:
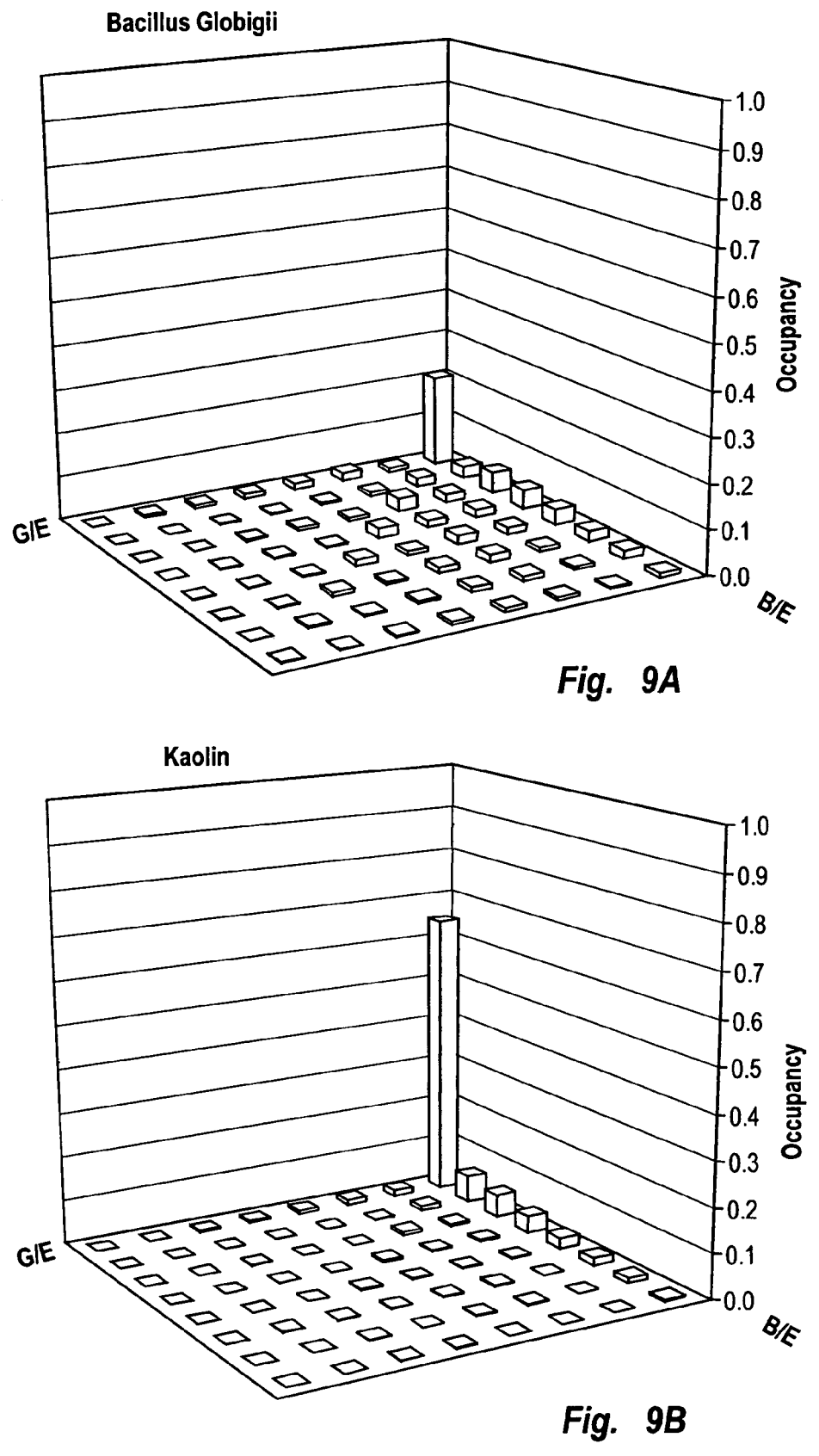

Thus, fluorescence space can be represented by an array. The array has D dimensions, n bins per dimension, for a total of $n^D$ bins. For example, FIG. 8 depicts an array for D=2 fluorescence channels, each with 6 levels, for a total of $6^2=36$ bins. Likewise FIG. 9A and FIG. 9B each depict arrays for two fluorescence channels, each with 8 levels. (Alternatively one may use fluorescence or other data channels that do not all have the same number of levels.)

The example uses several arrays, representing particle spectral distributions or counts. Those arrays are:

θ Spectral distribution of particles of interest, also called threat spectral distribution, threat distribution, threat array, or threat signature;

β Spectral distribution of particles in other samples, also called background spectral distribution, background array, or background signature;

Δβ Spectral distribution of current sample, also called the current sample spectral distribution or current sample distribution.

Each bin of an array can be identified by one level per dimension. Take for instance, a system with two fluorescence channels, one blue and one green. The bin of the background array representing particles with a normalized blue fluorescence of 2, and a normalized green fluorescence of 3 is represented by $\beta_{23}$. In general, each bin of β is represented by $\beta_{ij\ldots}$, where the number of subscripts equals D.

Initializing Background Spectral Probability Distribution

Method 350 may include the step 352 of initializing a background spectral probability distribution. Example method 350 may perform step 352 because the method may not yet have a known background particle signature. Step 352 involves sampling the background and determining the background signature based on those samples. (Alternatively, the method may start with a given initial background signature.)

Figure 5:
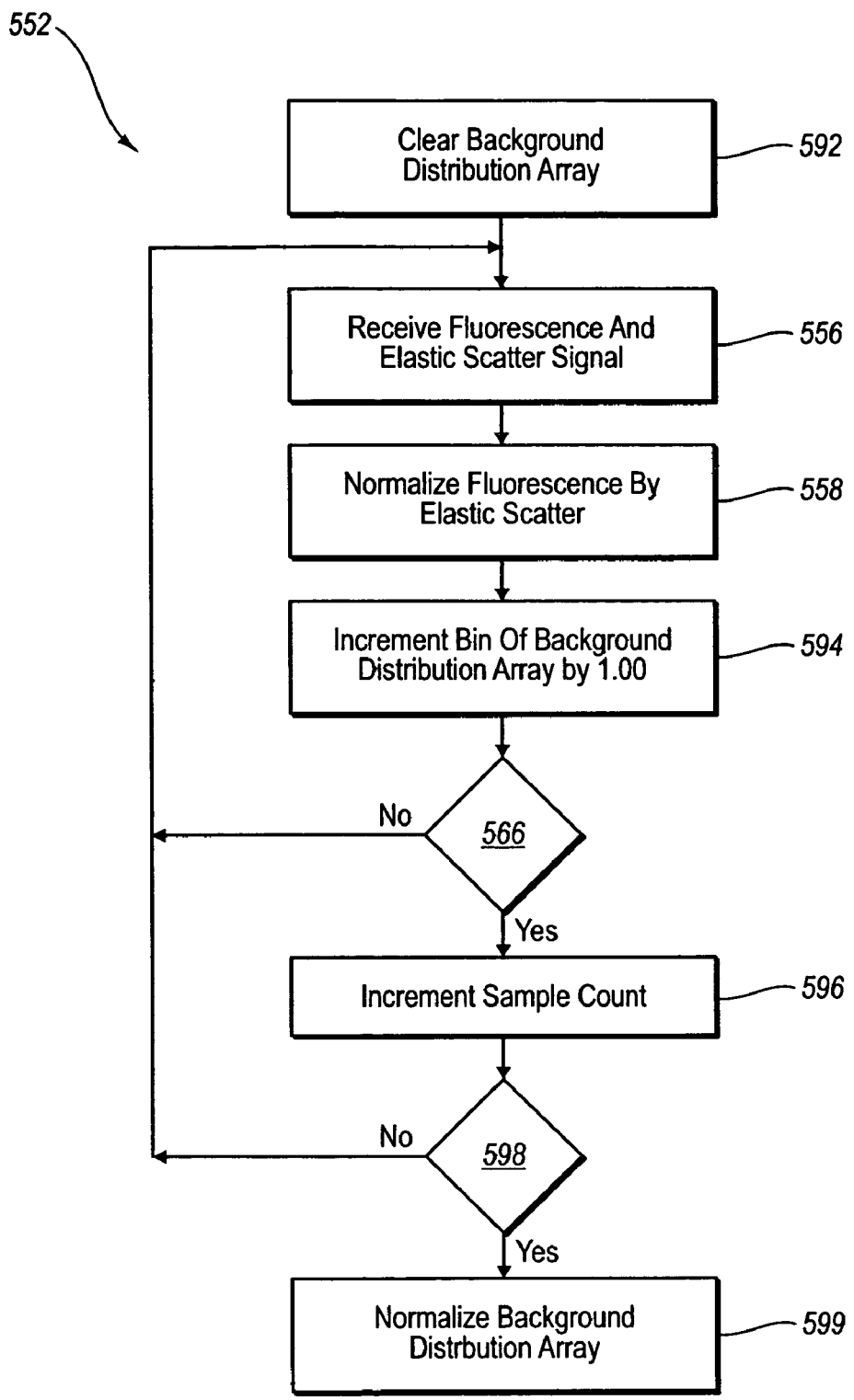
FIG. 5 is a flow diagram representing one embodiment of a method for initializing a background spectral probability distribution.

FIG. 5 is a flow diagram representing the details of one embodiment 552 of initializing the background signature, which was shown generally as step 352 of FIG. 3. When the sensor hardware is first initialized, it is assumed that only background particles are present. In this embodiment the sensor cannot decide whether the first sample is a sample of concern because the sensor must first establish a baseline of background particles. Thus, this embodiment should be booted during the absence of any threat particles.

During initialization 552, the sensor builds a spectral distribution in the background array β by acquiring particle data for a number of background samples. The sensor clears the background array β (step 592) and initializes a sample count to zero. (The sensor uses the sample count to keep track of how may samples it has processed.)

In step 556, the sensor receives fluorescence and elastic scatter data for a particle. The sensor may receive D fluorescence counts ($F_1, F_2, \ldots F_D$) and an elastic scatter level E.

The sensor may normalize fluorescence by elastic scatter E (step 558) according to the following equation 5.1:

$$i = \frac{KF_1}{E}; j = \frac{KF_2}{E} \qquad \text{Eq. 5.1}$$

In equation 5.1, each F value is scaled by a settable parameter K, i.e., an elastic normalization scaling constant, and divided by E. K scales the calculation such that each outcome i,j, ... is in the range of 0 to n−1 for most particles.

The outcomes may be limited so that they do not exceed n, the upper bound of the array. (Systems may use alternative normalizing, such as normalizing to unity.) Taken together, the normalized and scaled outcomes i,j, . . . correspond to a vector F and to a bin in background array β. One embodiment characterizes each particle by the fluorescence vector F=(B/E, G/E), where B is the PEC in the blue range of wavelengths and G is the PEC in the green range of wavelengths, and E is the elastic scatter. The components $F_k$ may be fluorescence photoelectron counts, fluorescence normalized to elastic scatter, or some other quantities.

Regarding the mesh size, the same bin allocation is typically used for threat probability distribution θ, background probability distribution β, and current sample distribution (Δβ). However, the bins need not be uniform in size. For example, when F space is unbounded, the outer bin(s) may be defined to extend to infinity. The bins may be defined to provide sufficient resolution of the threat distribution, but the mesh need not be particularly fine. In one embodiment, each dimension has five bins: one at the peak, one on each shoulder, and one on each tail of the probability distribution. The total number of bins is $5^D$: 625 for 4 fluorescence channels. This is small compared to the 30,000 or more particles typically populating a histogram, so sparse matrix problems may be avoided.

In step 594, the sensor may increment the bin of background array β corresponding to the vector F, as shown in equation 5.2:

$$\beta_{ij\,\ldots} = \beta_{ij\,\ldots} + 1 \qquad \text{Eq. 5.2}$$

In step 566 the sensor determines whether it has completed a sample. In this implementation, the sample is determined by the number of particles processed. N is number of particles per sample—a settable parameter. If the sensor has not yet processed N particles, the method continues to receive particle data (step 556), normalize fluorescence (558), and update the background distribution (step 594) for the next particle. By defining a sample based on the number of particles, the system may reduce the number of false positives caused by increases in background concentration. For instance, in a device that alarms on 100 threat particles per sample and that mistakes 1% of background particles for threat particles, setting the N=1000 means that about 90 real threat particles per 1000 must be present to cause an alarm, regardless of overall particle concentration. Alternatively, a sample may be determined by the acquisition of an undetermined number of particles for a fixed time period, by combinations of time and particle numbers, or by other methods.

At the end of a sample, the sensor increments the sample count (step 596). In step 598, the sensor determines if enough samples have been taken by seeing if the sample count is equal to the settable memory aging parameter (J), i.e., when J samples have been taken. If not, the sensor acquires more samples by looping back to step 556.

If J samples have been taken, each bin of background array β contains a count of the number of sample particles of each vector. The array may be normalized in step 599 by dividing the count in each bin by the total number of particles, according to equation 5.3.

$$\beta_{ij\,\ldots} = \frac{1}{J \cdot N} \beta_{ij\,\ldots} \quad \text{for each } i, j, \ldots \text{ in array } \beta \qquad \text{Eq. 5.3}$$

This normalization makes the sum of the bins of the background array β equal to 1. Thus, array β can be considered the spectral probability distribution, or signature, of the background particles.

The example may be given a threat signature θ or may be given data from which it may derive θ as part of initialization. Alternatively, the example may acquire the threat signature θ by sampling particles of interest in the absence of background particles, in a manner similar to the way it acquires the initial background signature β.

Unknown Sample Acquisition, Particle Weighting, and Sample Testing

After initialization, the example method may acquire samples of unknown particles, and determine if they are samples of interest. The example keeps track of the total weight of the particles in the current sample. The example method may also use an array Δβ—the current sample spectral distribution array—to represent the spectral distribution of particles in the current sample. It may use this array to update the background signature. In preparation for acquiring data for a sample, the example method may clear the current sample distribution array (Δβ) and set the total particle weight to zero. Furthermore, the sample count may be incremented depending on how many samples have been processed thus far.

Before the example tests any particular sample, it may compute a threshold or alarm level. It may also compute parameters to be used by the weighting function. According to one embodiment shown in FIG. 3, this step 354 involves computing various statistical measures, such as means, variances, and standard deviations. The fractional sensitivity parameter η may be determined by equation 3.1:

$$\eta = \frac{N_\theta}{2N} \qquad \text{Eq. 3.1}$$

where

N=the number of particles per sample, and $N_\theta$=the threat sensitivity or number of threat particles in the sample.

However, the number of threat particles in a sample is not necessarily exactly $N_\theta$, rather, it is a random variable $v_\theta$ that is binomially distributed about $N_\theta$. Because the sample size is exactly N, the number of background particles is $N-v_\theta$.

A denominator G of a weighting function is represented by the following equation 3.2 for all i,j . . . in threat array θ and background array β:

$$G = \left\langle \frac{(\theta_{ij\,\ldots} - \beta_{ij\,\ldots})^2}{\eta \theta_{ij\,\ldots} + (1-\eta)\beta_{ij\,\ldots}} \right\rangle \qquad \text{Eq. 3.2}$$

For N>>1, the probability distributions θ and β may be normal, and therefore may be characterized by a mean ($M_0$, $M_1$) and standard deviation ($S_0$, $S_1$). Equation 3.3 represents the mean of the threat-absent distribution ($M_0$):

$$M_0 = N \cdot \frac{1}{G} \cdot \left\langle \frac{(\theta_{ij\,\ldots} - \beta_{ij\,\ldots})\beta_{ij\,\ldots}}{\eta \theta_{ij\,\ldots} + (1-\eta)\beta_{ij\,\ldots}} \right\rangle \qquad \text{Eq. 3.3}$$

for all i,j, . . . in arrays θ and β.

The mean of the threat-present distribution ($M_1$) is calculated by equation 3.4:

$$M_1 = M_0 + N_\theta \qquad \text{Eq. 3.4}$$

The standard deviation of a threat-absent distribution ($S_0$) may be calculated from equation 3.5:

$$S_0^2 = N \cdot \frac{1}{G^2} \left\langle \left( \frac{\theta_{ij\ldots} - \beta_{ij\ldots}}{\eta \theta_{ij\ldots} + (1-\eta)\beta_{ij\ldots}} \right)^2 \beta_{ij\ldots} \right\rangle \qquad \text{Eq. 3.5}$$

for all i,j, . . . in arrays $\theta$ and $\beta$. The standard deviation, $S_0$, is the square root of the variance, $S_0^2$.

The standard deviation of a threat-present distribution ($S_1$) may be calculated from equations 3.6 and 3.7 as follows:

$$S_1^2 = \qquad \text{Eq. 3.6}$$
$$S_0^2 + N_\theta \cdot \frac{1}{G^2} \left\langle \left( \frac{\theta_{ij\ldots} - \beta_{ij\ldots}}{\eta \theta_{ij\ldots} + (1-\eta)\beta_{ij\ldots}} \right)^2 (\theta_{ij\ldots} - \beta_{ij\ldots}) \right\rangle$$

where $$S_1 = \sqrt{S_1^2} \qquad \text{Eq. 3.7}$$

The example computes the alarm level (A) by the following equation 3.8:

$$A = M_1 - \sqrt{2} S_1 \mathrm{erf}^{-1}[2P_d - 1] \qquad \text{Eq. 3.8}$$

where $P_d$ is the probability of detection, a settable parameter. In one embodiment, $P_d$ may be assumed to be greater than or equal to 0.5. The false positive rate (FPR) may be equal to the false positive probability ($P_-$) divided by the response time (T) and is related to the alarm level (A) as shown in equation 3.9:

$$FPR = \frac{P_-}{T} = \frac{1}{2T} \mathrm{erfc}\left( \frac{A - M_0}{\sqrt{2} S_0} \right) \qquad \text{Eq. 3.9}$$

where it may be assumed that $P_- \leq 0.5$. The response time (T) may be related to the sample size N by equation 3.10:

$$T = \frac{N}{CR\xi} \qquad \text{Eq. 3.10}$$

where C is the atmospheric particle concentration, R is the sampling volume flow rate, and $\xi$ is the efficiency of the particle concentrator. At this point, each of the four sensor metrics discussed above may be a control parameter or an output of the DoT process.

Receive Particle Data

The example sensor may now acquire fluorescence (i.e., the fluorescence PEC according to the embodiment of FIG. 1) and scattering data (step 356). Alternative data may be used as discussed above and as known to those skilled in the art. The example receives D fluorescence photoelectron counts ($F_1, F_2, \ldots F_D$) and one elastic scatter level E.

Normalize Particle Data and Characterize Particle

The system may perform step 358 of normalizing fluorescence by elastic scatter E and a scaling factor K, as discussed above in connection with initialization and Equation 5.1.

In step 360, the system characterizes each detected particle by a signal or vector F which may be fluorescence where $F = (F_1, F_2, \ldots F_D)$ or normalized fluorescence where $F = (KF_1/E, KF_2/E, \ldots KF_D/E)$. The bin corresponding to F of the current sample distribution ($\Delta\beta$) may then be incremented according to equation 3.12:

$$\Delta\beta_{ij\ldots} \ldots \Delta\beta_{ij\ldots} + 1 \qquad \text{Eq. 3.12}$$

Assign Weight

In step 362, the example assigns each particle a weight. This is done with a weighting function W(F) of the vector for the particle. The weight may be based on the particle vector, the threat-signature $\theta$, and the background signature $\beta$. The weighting function $W_0(F)$ may be a functional of both the threat probability distribution $\theta(F)$ and the background probability distribution $\beta(F)$. The weighting function may help distinguish between the hypothesis $H_0$ (there are no threat particles in the N-particle sample) and $H_1$ (there are $N_\theta$ threat particles present in the N-particle sample). The sensor may use other weighting functions.

One embodiment of $W_0$ may be derived by assuming initially that threat particles are absent. In an infinitesimal region $\delta F$, the number of particles may be a random variable that is Poisson distributed, and thus has an equal mean and variance given by equation 3.13:

$$\delta\mu = \delta\sigma^2 = N\beta(F)\delta F \qquad \text{Eq. 3.13}$$

The distribution of the differential weight of the region has a mean $W(F)\delta\mu$ and standard deviation $W(F)[\delta\sigma^2]^{1/2}$. Note that these are the corresponding parameters of the differential number distribution scaled by W, but the differential weight distribution may not be Poissonian, because its mean and variance are in general not equal.

The differential means and variances are then integrated over F, and the central limit theorem is invoked to conclude that $\wp(X|H_0)$ is normally distributed, with mean and variance represented by equations 3.14 and 3.15, respectively:

$$M_0 = N \langle W\beta \rangle \qquad \text{Eq. 3.14}$$

$$S_0^2 = N \langle W^2 \beta \rangle \qquad \text{Eq. 3.15}$$

where $$\langle Q \rangle = \oint_F dF Q(F)$$

for any function Q. $\qquad$ Eq. 3.16

Assuming that the mean fraction of threat particles is $N_\theta/N$, equations 3.13 through 3.16 yield the mean of the threat-present distribution of Equation 3.17, and the standard deviation of the threat-present distribution of Equation 3.18:

$$M_1 = (N - N_\theta)\langle W\beta \rangle + N_\theta \langle W\theta \rangle \qquad \text{Eq. 3.17}$$

$$S_1^2 = (N - N_\theta)\langle W^2 \beta \rangle + N_\theta \langle W^2 \theta \rangle \qquad \text{Eq. 3.18}$$

Based on the above, $\wp(X|H_0)$ and $\wp(X|H_1)$ are determined by quantities that are either prescribed or measurable. According to one embodiment, a convenient approximate technique to optimize W is to minimize the overlap integral 490 shown in FIG. 4B, as discussed generally above, according to equation 3.19:

$$\Phi \int_{-\infty}^{+\infty} dX \wp(X \mid H_0) \wp(X \mid H_1) = \quad \text{Eq. 3.19}$$

$$\frac{\exp\left[-\frac{[N_\theta \langle W(\theta-\beta) \rangle]^2}{2[2N \langle W^2 \beta \rangle + N_\theta \langle W^2(\theta-\beta) \rangle]}\right]}{\sqrt{1 + \frac{N_\theta \langle W^2(\theta-\beta) \rangle}{2N \langle W^2 \beta \rangle}}}$$

The weak dependence of $\Phi$ on the square root in the denominator is neglected in favor of the strong dependence on the exponential in the numerator. Thus, minimizing the overlap integral may be simplified to maximizing the absolute value of the argument of the exponential as represented in equation 3.20:

$$\Psi \equiv \frac{[N_\theta \langle W(\theta-\beta) \rangle]^2}{2[2N \langle W^2 \beta \rangle + N_\theta \langle W^2(\theta-\beta) \rangle]} \quad \text{Eq. 3.20}$$

$\Psi$ may be invariant with respect to the multiplicative scaling $W \rightarrow \alpha W$, where $\alpha$ is a real constant, because scaling the weighting function by some factor will not affect the results. So W may be normalized as indicated in equation 3.21:

$$\langle W(\theta-\beta) \rangle = 1 \quad \text{Eq. 3.21}$$

According to equation 3.21, the average threat particle weight is larger than the average background particle weight by unity. This also fixes the numerator of $\Psi$, allowing the further simplification of minimizing $\Phi$ by minimizing $\Gamma$ in equation 3.22:

$$\Gamma \equiv 2N \langle W^2 \beta \rangle + N_\theta \langle W^2(\theta-\beta) \rangle \quad \text{Eq. 3.22}$$

Using Lagrange's method of undetermined multipliers to minimize $\Gamma$, subject to the constraint expressed by equation 3.21, the weighting function $W_0$ is expressed by:

$$W_0 = \frac{\frac{\theta-\beta}{\eta\theta+(1-\eta)\beta}}{\left\langle \frac{(\theta-\beta)^2}{\eta\theta+(1-\eta)\beta} \right\rangle} \quad \text{where } \eta \equiv \frac{N_\theta}{2N} \quad \text{Eq. 3.23}$$

$W_0$ is a minimum because the second derivative of $\Gamma$ with respect to W is positive everywhere. $W_0$ is also unique because the two conditions from which it obtains are each linear, so that there is one solution.

Alternatively, the weighting function may be optimized using brute force techniques. It is also possible to define a weighting function that is not optimal or approximately optimal (in the sense of minimizing the overlap integral) but still substantially reduces the probability of false positives versus an optimally Region of Threat. For instance, FIG. 11 shows curves for hypothetical non-optimal DoT weighting functions. Those particular non-optimal curves have reduced false positive rates compared to an optimal Region of Threat approach, but higher false positive rates than the optimal DoT curve. And although the particular weighting function described above has been described mathematically, a weighting function need not be a mathematical function; it may be any "grey-scale" scheme that assigns weights to particles, such as a scheme created in advance, or empirically.

Cumulate Weights for the Sample

In step 364, the example adds the assigned weight W of each particle to the cumulative weight X of the sample. This is represented by equation 3.24:

$$X = X_0 + W \quad \text{Eq. 3.24}$$

Determine if Sample is Complete

After each particle is processed, the example determines 366 whether it has acquired a complete sample. One embodiment does this by seeing if it has processed N particles. A sensor may use an alternative test for sample completion, as discussed above in connection with initialization. If the sample is incomplete, the sensor may loop back to step 356, continuing to acquire and process particles until a sample is complete.

Decide if Sample Includes Requisite Level of Particles of Interest

In step 368, the example may compare the total weight X determined in step 364 to the threshold level computed in step 354 and decide whether the total weight exceeds the alarm level. Alternatively, the test also may be mathematically more complex. In the example, the comparison and decision are made once per sample. Alternatively, these steps could be performed more often (e.g., whenever cumulative weight is incremented) or less often (e.g., after every several samples).

If the total weight X exceeds the threshold then, in step 370, the method may issue an alarm. This may be an alarm signal that is acted upon by software, hardware, or a combination of both. It may be a humanly perceptible signal, such as an audible alarm. The alarm may be coupled with another function, such as sealing a duct system where the pathogen detection system is located. The method 350 may use any type of response indicating whether the requisite number of particles of interest are present, or any type of response to a decision whether a sample more likely reflects one population's distribution versus another population's distribution.

Background Update

If the total weight of the sample does not exceed the alarm level, then the sensor may consider the sample to be a component of background probability distribution and the system will updated the background probability distribution (step 372). This updating is discussed in greater detail in conjunction with FIG. 6.

Figure 6:
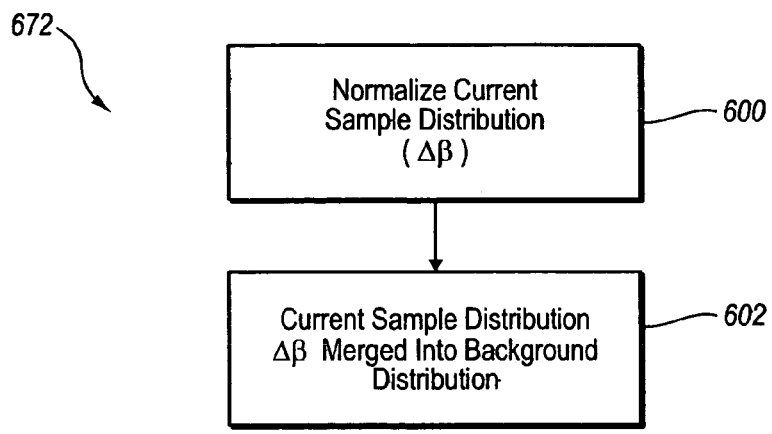
FIG. 6 is a flow diagram representing one embodiment of a method for updating a background according to the method for processing the signal as shown in FIG. 3.

FIG. 6 is a flow diagram representing one embodiment of updating 672 a background. The sensor updates the background signature $\beta$ is to include the current sample probability signature $\Delta\beta$. In this embodiment, current sample signature $\Delta\beta$ does not replace background signature $\beta$, but instead is blended in. In step 600, the sensor normalizes 600 the current sample signature $\Delta\beta$ such that the sum of all its bins is 1, as expressed in equation 6.1:

$$\Delta\beta_{ij\ldots} = \frac{1}{N} \Delta\beta_{ij\ldots}$$

In step 602, the sensor may merge the normalized current sample signature $\Delta\beta$ into the background signature (which was normalized in step 599) according to a settable aging parameter J using equation 6.2:

$$\beta_{ij\ldots} = \left[1 - \frac{1}{J}\right]\beta_{ij\ldots} + \frac{1}{J}\Delta\beta_{ij\ldots}$$

After (a) indicating that the present sample contains the requisite amount of particles of interest, or (b) updating the background signature, the sensor may test subsequent samples by looping back to step 354.

The steps in this method may be performed in different orders. Also, steps represented in one block of a flow diagram may be performed wholly or partly in a different block of the same flow diagram, or in a different flow diagram. For instance, the sensor may calculate the weighting function for each possible vector F before acquiring any data for a sample.

Computing Device

Figure 7:
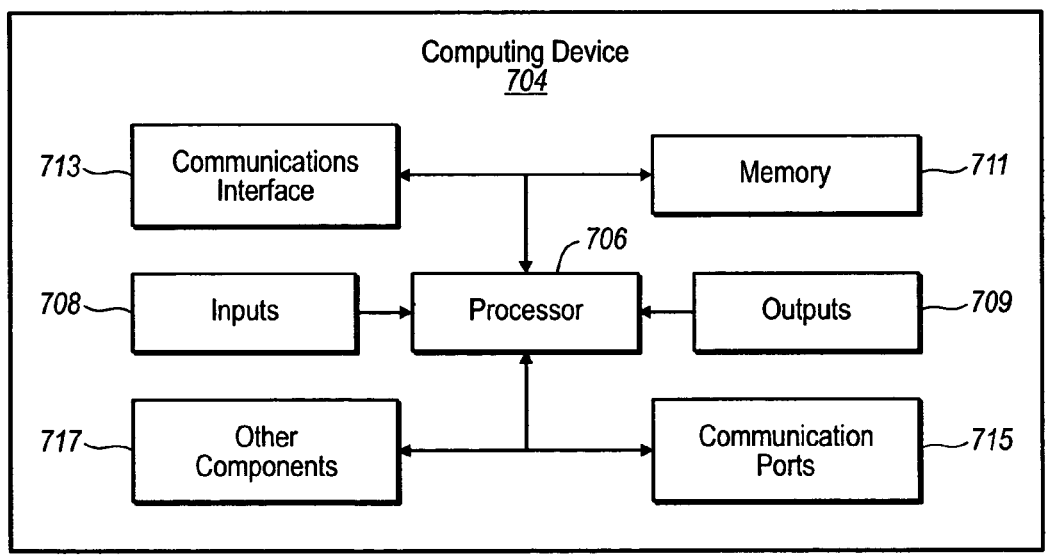
FIG. 7 is block diagram illustrating the major hardware components typically used in a computing device used in conjunction with a system for detecting a concentration of hazardous particles against a background of harmless particles.

FIG. 7 is a block diagram showing major hardware components of a typical computing device 704 used in conjunction with a system for detecting particles of interest against a background of other particles. Computing devices 704 are known in the art and are commercially available. A computing device 704 typically includes a processor 706 in electronic communication with input components 708 and/or output components 709. The processor 706 is operably connected to input 708 and/or output components 709 capable of electronic communication with the processor 706, or, in other words, to devices capable of input and/or output in the form of an electrical signal. Embodiments of computing devices 704 may include the inputs 708, outputs 709 and the processor 706 within the same physical structure or in separate housings or structures.

The computing device 704 may also include memory 711. The memory 711 may be a separate component from the processor 706, or it may be on-board memory included in the same part as the processor. For example, microcontrollers often include a certain amount of on-board memory.

The processor 706 is also in electronic communication with a communication interface 713. The communication interface 713 may be used for communications with other devices, such as other computing devices. The computing device 704 may also include other communication ports 715. Computing device 704 may include other components 717.

Those skilled in the art will appreciate the many kinds of different devices that may be used with embodiments herein. The computing device 704 may be a one-board type of computer, such as a controller, a typical desktop computer, such as an IBM-PC compatible, a PDA, a Unix-based workstation, or any other available computing device that is capable of operating the algorithms and methods disclosed herein. Accordingly, FIG. 7 is only meant to illustrate typical components of a computing device 704 and not to limit the scope of embodiments disclosed herein.

Those skilled in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the appended claims.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The methods disclosed herein comprise one or more steps or actions for achieving the described method. The method steps and/or actions may be interchanged with one another. In other words, unless a specific order of steps or actions is required for proper operation of the embodiment, the order and/or use of specific steps and/or actions may be modified. The scope of the present invention should, therefore, be determined only by the following claims.

The invention claimed is:

1. A method of using laser-induced fluorescence to distinguish (a) a presence of threat particles interspersed with background particles from (b) an absence of threat particles, the threat particles representing fluorescent biological substances, comprising:

using a multiple-wavelength detection-band laser-induced fluorescence sensor to acquire a measurement set of particles for laser-induced fluorescence analysis, the sensor providing threat-present and threat-absent particle signals in response to the acquired measurement set of particles;

defining a grey-scale weighting function formulated on competing sensitivity and false positive rate factors, the sensitivity factor representing sensitivity of detecting threat particles against non-threat particles and the false positive rate factor representing a probability of falsely concluding that the acquired measurement set of particles contains threat particles;
using the weighting function to assign weights to particles in the measurement set, based on a numerical characterization of a particle and a weight associated with that characterization;
assigning weights to each particle in the measurement set, based on the weighting function; and
processing the weights assigned to the particles and producing an indication whenever a result obtained from the processing of the weights represents a likelihood of concluding correctly that the measurement set of particles contains threat particles.

2. The method of claim 1, in which the threat-present and threat-absent particle signal distributions exhibit an overlapping region, further comprising optimizing the weighting function to diminish the overlapping region.

3. The method of claim 1, in which the processing includes accumulating the weights assigned to the particles, and in which the result of the process is an accumulated weight that produces the indication.

4. The method of claim 3, in which the threat-present and threat-absent particle signal distributions exhibit an overlapping sum of weights distributions, wherein the method further comprises optimizing the weighting function by substantially minimizing an overlap integral of the threat-present and threat-absent sum of weights distributions.

5. The method of claim 3, in which the weighting function is derived from a pre-determined fluorescence-space distribution of threat particles and from a distribution of background particles that adapts to a changing background.

6. A method of deciding whether a particle-containing sample of an air stream, which air stream may contain particles of interest and background particles, is a sample of interest, comprising:
detecting a measurement set of particles in the air stream;
defining a numerical characterization scheme for characterizing particles in the measurement set;
individually assigning a numerical characterization to each detected particle in the measurement set;
defining a grey-scale weighting function, with a range of more than two weights, capable of associating a weight with a numerical characterization;
using the weighting function in assigning weights to particles in the measurement set, based on the numerical characterization of a particle and the weight associated with that characterization;

processing the assigned weights for detected particles in a sample; and producing an indication, based on the processing of the assigned weights, whether the measurement set contains some particles of interest or background particles.

7. The method of claim 6 in which:

the indication has (a) a sample-of-interest distribution which characterizes the distribution of processed particle weights of samples of interest; and (b) a background distribution of which characterizes the distribution of processed particle weights of background samples; and wherein the weighting function is a function of the sample-of-interest distribution and a function of the background distribution.

8. The method of claim 7 in which:

the sample-of-interest distribution has an overlap with the background distribution; and the weighting function assigns weights to reduce the overlap.

9. The method of claim 8 in which:

the sample-of-interest distribution has a mean and a variance;

the background distribution has a mean and a variance; and the weighting function assigns weights to substantially maximize (a) the squared difference of the means of (i) the sample-of-interest distribution and (ii) the background distribution, divided by (b) a sum of the variances of (i) the sample-of-interest distribution and (ii) the background distribution.

10. The method of claim 9 in which:

the difference of the means of (i) the sample-of-interest distribution and (ii) the background distribution is held constant by exploiting an invariance of results to multiplicative scaling of the weighting function; and the weighting function assigns weights to substantially minimize the sum of the variances of (a) the sample-of-interest distribution and (b) the background distribution.

11. The method of claim 10 in which:

minimizing the sum of the variances of (a) the sample-of-interest distribution and (b) the background distribution is performed using Lagrange's method of undetermined multipliers.

12. The method of claim 6 in which:

the weighting function is based on a particle-weight distribution of background particles and on a particle-weight distribution of particles of interest.

13. The method of claim 12 in which the particles of interest are aerosolizable pathogen particles.

14. A device for analyzing samples of an air stream containing particles, comprising:

an excitation wavelength;

an emission wavelength that is different from the excitation wavelength;

an illumination area through which the air stream passes;

a light source, comprising light at the excitation wavelength, that illuminates, in the illumination area, the particles contained in the air stream;

an excitation light detector that detects light from the particles at the excitation wavelength;

a fluorescence detector that detects light at the emission wavelength;

a memory that accumulates particle information, including (a) data representing a count of a number of particles that has passed through the illumination area and (b) data representing light detected by the fluorescence detector;

a sample-size criterion comprising data representing a maximum number of particles to be included in a complete sample, the complete sample comprising a plurality of particles; and a sample-completion testing module that applies the sample-size criterion to determine when the memory has accumulated particle data from a complete sample.

15. The device of claim 14 in which the sample-size criterion further comprises information representative of a time interval.

16. The device of claim 14 in which the maximum number of particles to be included in a complete sample is predetermined.

17. The device of claim 14 in which the particle information accumulated in the memory comprises data representative of light from the particles that has been detected by the excitation detector.

18. A system for reducing the false positives in a particle detection system, comprising:
- a laser that irradiates a particle-containing airstream containing unknown particles which may be particles of interest or background particles;
- a fluorescence detector that detects fluorescence emitted by the particles in the airstream in response to irradiation by the laser;
- a non-fluorescence detector that detects particles in the airstream regardless of fluorescence;
- a computer-readable medium for storing:
  - a sample size, expressible or convertible into in time, to determine a size of a sample of detected particles a sample volume rate expressible in liters per second;
  - a sensitivity expressible by a number of *Bacillus globigii* particles amid a number of total particles per volume;
  - a mean time between false positives; and
  - a true positive confidence level;
  - where a common log of the mean time in seconds between false positives is greater than 4 for a true positive confidence level of 90% and a sample time, sensitivity, and true positive confidence level for conditions with ratios of: (a) 10 seconds, to (b) a ratio of 42 *Bacillus globigii* particles per 2500 total particles per liter.

19. The system of claim 18 in which the common log of the mean time between false positives is greater than 5.

20. The system of claim 18 in which the common log of the mean time between false positives is greater than 6.

21. The system of claim 18 in which the common log of the mean time between false positives is greater than 7.

* * * * *